(12) United States Patent
Wu et al.

(10) Patent No.: US 6,784,293 B1
(45) Date of Patent: Aug. 31, 2004

(54) PROCESS FOR MAKING BOC-PROTECTED 3-AMINOHYDANTOINS/THIOHYDANTOINS AND 3-AMINODIHYDROURACILS/DIHYDROTHIOURACILS

(75) Inventors: Shengde Wu, West Chester, OH (US); John Michael Janusz, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/089,329

(22) PCT Filed: Oct. 5, 2000

(86) PCT No.: PCT/US00/27503

§ 371 (c)(1),
(2), (4) Date: Jun. 25, 2002

(87) PCT Pub. No.: WO01/27087

PCT Pub. Date: Apr. 19, 2001

Related U.S. Application Data

(60) Provisional application No. 60/158,660, filed on Oct. 8, 1999.

(51) Int. Cl.$^7$ .................... C07D 233/80; C07D 233/86; C07D 239/22
(52) U.S. Cl. ................. 544/282; 544/310; 544/311; 544/312; 546/84; 546/121; 546/210; 546/274.4; 548/154; 548/302.7; 548/312.1; 548/312.7; 548/313.7; 548/314.7; 548/318.1
(58) Field of Search .................. 544/282, 310, 544/311, 312; 546/84, 121, 210, 274.4; 548/154, 302.7, 312.1, 312.7, 313.7, 314.7, 318.1

(56) References Cited

PUBLICATIONS

Wu et al., Solid–phase synthesis of 3–aminohydantoi, dihydruracil, thiohydantoin and dihydrouracil derivatives, Tetrahedron Letters, 41(8), pp. 1165–1169, 2000.*
Wu et al., An efficient one–pot synthesis of 3–aminohydantoin and 3–aminodihydruracil derivatives, Tetrahedron Letters, 41(8), pp. 1159–1163, 2000.*
Yoon, J. et al., "Solution and soluble polymer syntheses of 3–aminoimidazoline–2,4–diones", Chem. Commun., 1998, pp. 2703–2704.
Saegusa, Y. et al., "Reaction of 1,3,4–Oxadiazolones with Free L–α–Amino Acids: A Facile Syntheses of Novel 3,5–Disubstituted Hydantoins", J. of Heterocyclic Chem., 1990, vol. 27, No. 3, pp. 739–742.
Veverka M. et al., "Addition–Cyclization Reactions of Ethyl Isothiocyanatoacetate with Carboxylic Acid Hydrazides", Collection of Czechoslavak Chem. Communications, Academic Press, London, 1987, vol. 52, No. 1, pp. 113–119.
Murphy A.M. et al., "Automated synthesis of Peptide C–Terminal Aldehydes", J. of the Amer. Chem. Soc., 1992, vol. 114, No. 8, pp. 3156–3157.

* cited by examiner

Primary Examiner—Deepak Rao
(74) Attorney, Agent, or Firm—Richard S. Echler, Sr.; David V. Upite; James C. Kellerman

(57) ABSTRACT

The present invention provides a process for the efficient assembly of Boc-protected 3-aminohydantoins/thiohydantoins and 3-aminodihydrouracils/dihydrothiouracils via a one-pot solution phase or solid phase synthesis from readily available starting materials.

25 Claims, No Drawings

US 6,784,293 B1

PROCESS FOR MAKING BOC-PROTECTED 3-AMINOHYDANTOINS/THIOHYDANTOINS AND 3-AMINODIHYDROURACILS/ DIHYDROTHIOURACILS

This application is a 371 of PCT/US00/27503 filed Oct. 5, 2000 which claims the benefit of Provisional Application No. 60/158,660 filed Oct. 8, 1999.

TECHNICAL FIELD

The present invention is directed to a process for the efficient solution and solid-phase synthesis of Boc-protected 3-aminohydantoins/thiohydantoins and 3-aminodihydrouracils/dihydrothiouracils.

BACKGROUND OF THE INVENTION

The present invention is directed to a novel process for synthesizing Boc-protected 3-aminohydantoins, 3-aminodihydrouracils, and their thio-substituted counterparts using a one-pot solution-phase or solid-phase process. 3-aminohydantoin and 3-aminodihydrouracil derivatives are useful in both the pharmaceutical and agrochemical industries. For example, compounds containing the 3-aminohydantoin or 3-aminodihydrouracil nucleus are useful as anticonvulsant agents, antibacterial agents, metalloprotease inhibitors, diuretic agents, and pesticides.

Synthetic routes for the preparation of 3-aminohydantoin derivatives are disclosed in the following references: Kiec-Kononowicz, K.; Zejc, A.; Byrtus, H. *Pol. J. Chem.* 1984, 58, 585. Lange, J. et al. Polish Patent, PL 123138 B1, Apr. 30, 1984. Wright, G. C.; Michels, J. G.; Spencer, C. F. *J. Med. Chem.* 1969, 12, 379–381. Bernard, L. et al. French Patent, 2000801, Jan. 24, 1969. Kobayashi, N. et al. Japanese Patent, 09176131 A2, Jul. 8, 1997. Taub, W. U.S. Pat. No. 2,767,193, 1956. *Chem. Abstr.*, 1957, 51, 5811. Szczepanski, H.; Kristinsson, H.; Maienfish, P.; Ehrenfreund, J. WO 95/18123, 1995. Lindemann, A.; Khan, N. H.; Hoffmann, K. *J. Am. Chem. Soc.*, 1952, 74, 476–479. Gante, J.; Lautsch, W. *Chem. Ber.*, 1964, 97, 994. Schlogl, K.; Derkosch, J.; Korger, G. C. *Monatsh. Chem.* 1954, 85, 607. Schlogl, K.; Korger, G. *Monatsh. Chem.* 1951, 82, 799. Davidson, J. S. *J. Chem. Soc.* 1964, 4646–4647. Gillis, B. T.; Dain, J. G. *J. Heterocyclic Chem.* 1971, 8, 339–339. Wildonger, R. A; Winstead, M. B. *J. Heterocyclic Chem.* 1967, 4, 981–982. Lalezari, I. *J. Heterocyclic Chem.* 1985, 22, 741–743. Saegusa, Y.; Harada, S.; Nakamura, S. *J. Heterocyclic Chem.* 1990, 27, 739–742. Milcent, R.; Akhnazarian, A.; Lensen, N. *J. Heterocyclic Chem.* 1996, 33, 1829–1833. Ragab, F. A.; Eid, N. M.; El-Tawab, H. A. *Pharmazie* 1997, 52 (12), 926–929. Yoon, J; Cho, C-W; Han; H; Janda, K. D. *Chem. Comm.* 1998, 2703–2704. However, in general the synthetic routes disclosed above involve multiple steps, require harsh reaction conditions, and/or produce relatively low yields.

Additionally, there has been growing interest in the development of solid-phase synthetic approaches to hydantoin and dihydrouracil derivatives, particularly those substituted at the N-1, N-3, and C-5 positions. Syntheses of 1-aminohydantoins and 3-aminohydantoins by solid-phase synthetic approaches are disclosed in the following references: Dewitt, S. H.; Kiely, J. S.; Stankovic, C. J.; Schroder, M. C.; Reynolds Cody, D. M.; Pavia, M. R. *Proc. Natl. Acad. Sci.* 1993, 90, 6909–6913. Dressman, B. A.; Spangle, L. A.; Kaldor, S. W. *Tetrahedron Lett.* 1996, 37, 937–940. Hanessisan, S.; Yany, R.-Y. *Tetrahedron Lett.* 1996, 37, 5835–5838. Kim, S. W.; Ahn, S. Y.; Koh, J. S.; Lee, J. H.; Ro, S.; Cho, H. Y. *Tetrahedron Lett.* 1997, 38, 4603–4606. Matthews, J.; Rivero, R. A. *J. Org. Chem.* 1997, 62, 6090–6092. Gong, Y-D.; Najdi, S.; Olmstead, M. M.; Kurth, M. J. *J. Org. Chem.* 1998, 63, 3081–3086. Xiao, X.; Ngu, K.; Chao, C.; Patel, D. V. *J. Org. Chem.* 1997, 62, 6968–6973. Smith, J.; Liras, J. L.; Schneider, S. E.; Anslyn, E. V. J. *J. Org. Chem.* 1996, 61, 8811–8813. Sim, M. M.; Ganesan, A. *J. Org. Chem.* 1997, 62, 3230–3233. Wilson, L. J.; Li, M.; Portlock, D. E. *Tetrahedron Lett.* 1998, 39, 5135–5138. Hamuro, Y.; Marshall, W. J.; Scialdone, M. A. *J. Comb. Chem.* 1999, 1, 163–167.

There is a continuing need for improved processes for producing 3-aminohydantoins, 3-aminodihydrouracils, and their thio-substituted counterparts.

SUMMARY OF THE INVENTION

The present invention provides a process for the efficient assembly of Boc-protected 3-aminohydantoins/thiohydantoins and 3-aminodihydrouracils/dihydrothiouracils via a one-pot solution phase or solid phase synthesis from readily available starting materials.

DETAILED DESCRIPTION OF THE INVENTION

Definitions and Usage of Terms

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches. Unsaturated alkyl have one or more double bonds and/or one or more triple bonds. Alkyl chains may be unsubstituted or substituted with from 1 to about 4 substituents unless otherwise specified.

"Aromatic ring" is a benzene ring or a naphthlene ring.

"Carbocyclic ring" is a saturated or unsaturated hydrocarbon ring. Carbocyclic rings are not aromatic. Carbocyclic rings are monocyclic, or are fused, spiro, or bridged bicyclic ring systems. Monocyclic carbocyclic rings contain from about 4 to about 10 carbon atoms, preferably from 4 to 7 carbon atoms, and most preferably from 5 to 6 carbon atoms in the ring. Bicyclic carbocyclic rings contain from 8 to 12 carbon atoms, preferably from 9 to 10 carbon atoms in the ring. Carbocyclic rings may be unsubstituted or substituted with from 1 to about 4 substituents on the ring.

"Heteroatom" is a nitrogen, sulfur, or oxygen atom. Groups containing more than one heteroatom may contain different heteroatoms. As used herein, halogens are not heteroatoms.

"Heterocyclic ring" is a saturated or unsaturated ring containing carbon and from 1 to about 4 heteroatoms in the ring. Heterocyclic rings are not aromatic. Heterocyclic rings are monocyclic, or are fused or bridged bicyclic ring systems. Monocyclic heterocyclic rings contain from about 4 to about 10 member atoms (carbon and heteroatoms), preferably from 4 to 7, and most preferably from 5 to 6 member atoms in the ring. Bicyclic heterocyclic rings contain from 8 to 12 member atoms, preferably 9 or 10 member atoms in the ring. Heterocyclic rings may be unsubstituted or substituted with from 1 to about 4 substituents on the ring.

"Heteroaromatic ring" is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. Bicyclic heteroaromatic rings are ring systems wherein at least one of the two rings is a heteroaromatic ring and the other ring is a heteroaromatic ring, an aromatic ring, a carbocyclic ring, or a heterocyclic ring. Heteroaromatic rings may be unsubstituted or substituted with from 1 to about 4 substituents on the ring.

"Member atom" refers to a polyvalent atom (C, O, N, or S atom) in a chain or ring system that continues the chain or ring system. For example, in benzene the six carbon atoms are member atoms and the six hydrogen atoms are not member atoms.

Compounds Prepared Using the Present Process

The present invention is directed to a one-pot, solution-phase process for making Boc-protected 3-aminohydantoins/thiohydantoins and 3-aminodihydrouracils/dihydrothiouracils according to Formula I below:

Formula I

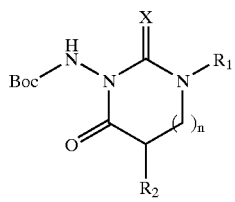

In Formula I above, X is O or S.

In Formula I above, n is 0 or 1.

In Formula I above, $R_1$ is H, alkyl, carbocyclic ring, heterocyclic ring, aromatic ring, or heteroaromatic ring. When $R_1$ is substituted alkyl, preferred substituents include: halo, hydroxy, alkoxy, aryloxy, acyloxy, carboxy, mercapto, alkylthio, arylthio, acylthio, carbamoyl, amido, aromatic ring, heteroaromatic ring, carbocyclic ring, and heterocyclic ring.

In Formula I above, $R_2$ is H, alkyl, carbocyclic ring, heterocyclic ring, aromatic ring, or heteroaromatic ring. When $R_2$ is substituted alkyl, preferred substituents include: halo, hydroxy, alkoxy, aryloxy, acyloxy, carboxy, alkoxycarbonyl, mercapto, alkylthio, arylthio, acylthio, amino, carbamoyl, carbamoyloxy, amido, alkoxylamido, ureido, guanidino, aryl, heteroaryl, cycloalkyl or heterocyclyl.

In Formula I above, when n is 0, $R_1$ and $R_2$ may instead together form a ring system; said ring system being carbocyclic ring, heterocyclic ring, or heteroaromatic ring. When n is 1, $R_1$ and the member carbon atom adjacent to the carbon atom containing $R_2$ may instead together form a ring system; said ring system being carbocyclic ring, heterocyclic ring, or heteroaromatic ring.

The Boc-protected 3-aminohydantoins/thiohydantoins and 3-aminodihydrouracils/dihydrothiouracils of the present invention may be further modified into substituted 3-aminohydantoins/thiohydantoins and 3-aminodihydrouracils/dihydrothiouracils using methods known to one of ordinary skill in the art.

Compounds which may be prepared using the present invention include, but are not limited to the following:

Carbamic acid, [2,5-dioxo-3-(phenylmethyl)-1-imidazolidinyl]-, 1,1-dimethylethyl ester.

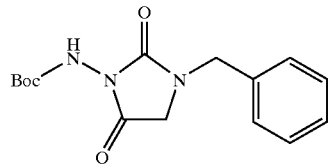

Carbamic acid, [5-oxo-3-(phenylmethyl)-2-thioxo-1-imidazolidinyl]-, 1,1-dimethylethyl ester.

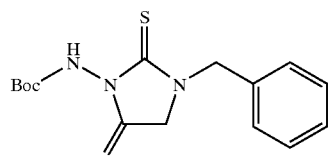

Carbamic acid, [4-methyl-2,5-dioxo-3-(phenylmethyl)-1-imidazolidinyl]-, 1,1-dimethylethyl ester.

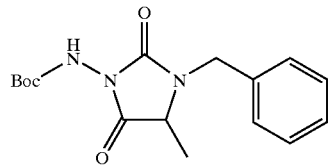

Carbamic acid, [4-methyl-5-oxo-3-(phenylmethyl)-2-thioxo-1-imidazolidinyl]-, 1,1-dimethylethyl ester.

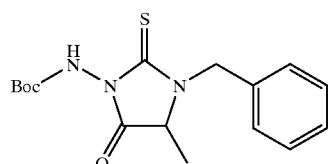

Carbamic acid, ((7aS)-tetrahydro-1,3-dioxo-1H-pyrrolo[1,2-c]imidazol-2(3H)-yl-, 1,1-dimethylethyl ester.

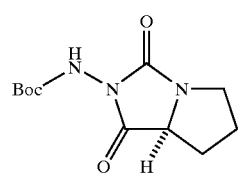

Carbamic acid, ((7aS)-tetrahydro-1-oxo-3-thioxo-1H-pyrrolo[1,2-c]imidazol-2(3H)-yl-, 1,1-dimethylethyl ester.

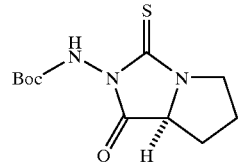

Carbamic acid, (Hexahydro-1,3-dioxoimidazol[1,5-a]pyridin-2(3H)-yl)-, 1,1-dimethylethyl ester.

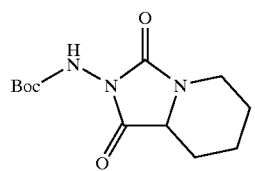

Carbamic acid, (Hexahydro-1-oxo-3-thioxoimidazol[1,5-a]pyridin-2(3H)-yl)-, 1,1-dimethylethyl ester.

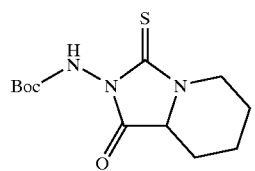

Carbamic acid, ((10aS)-1,5,10,10a-tetrahydro-1,3-dioxoimidazol[1,5-b]isoquinolin-2(3H)-yl)-, 1,1-dimethylethyl ester.

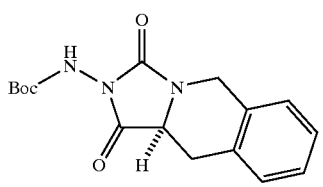

Carbamic acid, ((10aS)-1,5,10,10a-tetrahydro-1-oxo-3-thioxoimidazol[1,5-b]isoquinolin-2(3H)-yl)-, 1,1-dimethylethyl ester.

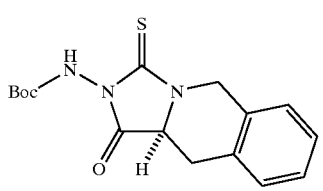

Carbamic acid, (Tetrahydro-5,7-dioxoimidazol[5,1-b]thiazol-6(5H)-yl)-, 1,1-dimethylethyl ester.

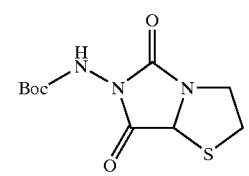

Carbamic acid, (Tetrahydro-7-oxo-7-thioxoimidazol[5,1-b]thiazol-6(5H)-yl)-, 1,1-dimethylethyl ester.

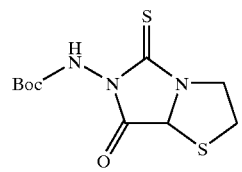

Carbamic acid, ((6R,7aS)-tetrahydro-6-hydroxy-1,3-dioxo-1H-pyrrolo[1,2-c]imidazol-2(3H)-yl-, 1,1-dimethylethyl ester.

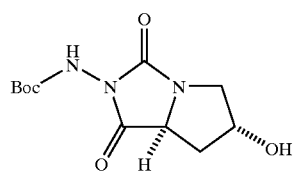

Carbamic acid, (2,5-dioxo-3-phenyl-1-imidazolidinyl)-, 1,1-dimethylethyl ester.

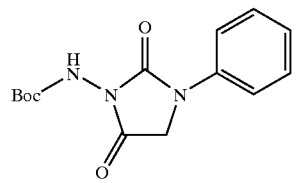

Carbamic acid, (5-oxo-3-phenyl-2-thioxo-1-imidazolidinyl)-, 1,1-dimethylethyl ester.

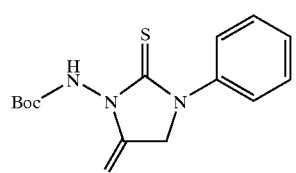

Carbamic acid, (tetrahydro-2,6-dioxo-3-(phenylmethyl)-1(2H)-pyrimidinyl)-, 1,1-dimethylethyl ester.

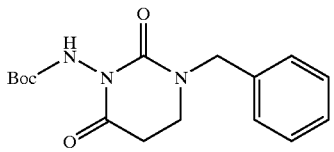

Carbamic acid, (tetrahydro-6-oxo-3-(phenylmethyl)-2-thioxo-1(2H)-pyrimidinyl)-, 1,1-dimethylethyl ester.

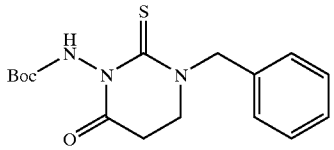

Carbamic acid, (3-(2-furanylmethyl)tetrahydro-2,6-dioxo-1(2H)-pyrimidinyl)-, 1,1-dimethylethyl ester.

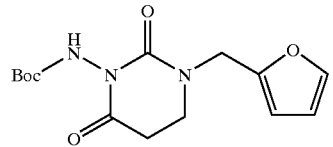

Carbamic acid, (3-(2-furanylmethyl)tetrahydro-6-oxo-2-thioxo-1(2H)-pyrimidinyl, 1,1-dimethylethyl ester.

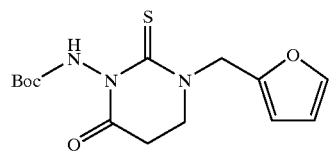

Carbamic acid, (3-butyltetrahydro-2,6-dioxo-1(2H)-pyrimidinyl)-, 1,1-dimethylethyl ester.

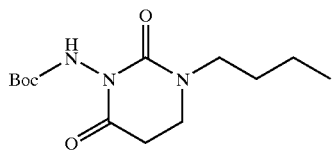

Carbamic acid, (3-butyltetrahydro-6-oxo-2-thioxo-1(2H)-pyrimidinyl-, 1,1-dimethylethyl ester.

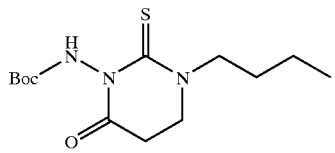

Carbamic acid, (tetrahydro-6-oxo-3-phenyl-2-thioxo-1(2H)-pyrimidinyl)-, 1,1-dimethylethyl ester.

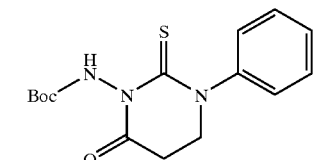

Carbamic acid, (tetrahydro-6-oxo-3-(4-methoxyphenyl)-2-thioxo-1(2H)-pyrimidinyl)-, 1,1-dimethylethyl ester.

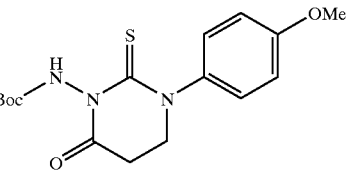

Carbamic acid, (hexahydro-1,6,8-trioxo-2H-pyrazino[1,2-c]pyrimidin-7(6H)-yl-, 1,1-dimethylethyl ester.

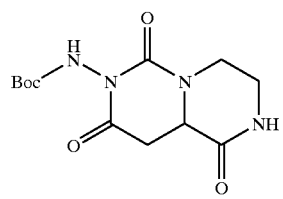

Carbamic acid, [3-[(4-methoxyphenyl)methyl]-2,5-dioxo-1-imidazolidinyl]-, 1,1-dimethylethyl ester.

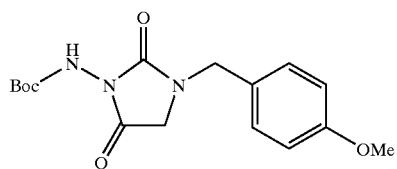

Carbamic acid, [3-(1,3-benzodioxol-5-ylmethyl)-2,5-dioxo-1-imidazolidinyl]-, 1,1-dimethylethyl ester.

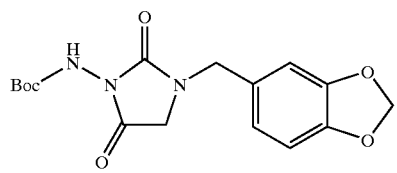

Carbamic acid, [2,5-dioxo-3-[2-(2-pyridinyl)ethyl]-1-imidazolidinyl]-, 1,1-dimethylethyl ester.

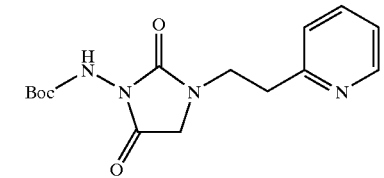

Carbamic acid, [3-[2-(5-methoxy-1H-indol-3-yl)ethyl]-2,5-dioxo-1-imidazolidinyl]-, 1,1-dimethylethyl ester.

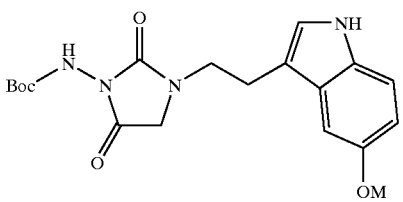

Carbamic acid, [3-[2-(1H-imidazol-4-yl)-ethyl]-2,5-dioxo-1-imidazolidinyl]-, 1,1-dimethylethyl ester.

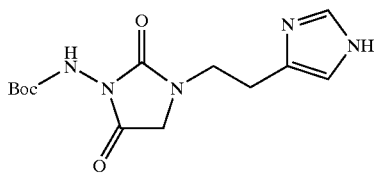

Carbamic acid, [3-[2-(1H-imidazol-1-yl)-ethyl]-2,5-dioxo-1-imidazolidinyl]-, 1,1-dimethylethyl ester.

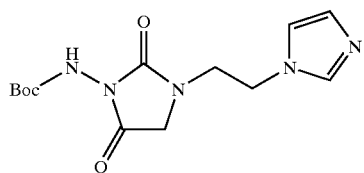

Carbamic acid, [3-[2-[[5-nitro-2-pyridinyl]amino]ethyl]-2,5-dioxo-1-imidazolidinyl]-, 1,1-dimethylethyl ester.

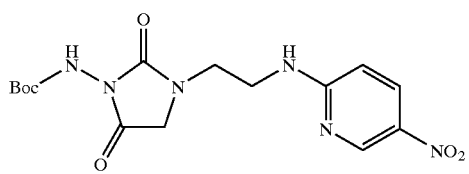

Carbamic acid, [2,5-dioxo-3-[2-(1-piperidinyl)ethyl]-1-imidazolidinyl)-, 1,1-dimethylethyl ester.

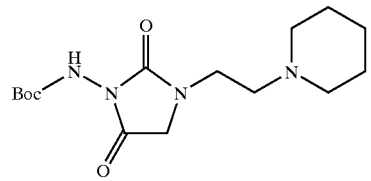

Carbamic acid, [5-oxo-3-[2-(1-piperidinyl)ethyl]-2-thioxo-1-imidazolidinyl]-, 1,1-dimethylethyl ester.

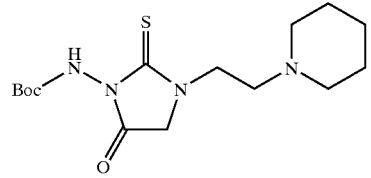

Carbamic acid, [3-[2-(1-methyl-2-pyrrolidinyl)ethyl]-2,5-dioxo-1-imidazolidinyl]-, 1,1-dimethylethyl ester.

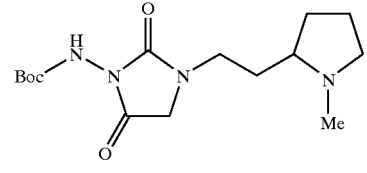

Carbamic acid, [3-[2-(2-methyl-1-piperidinyl)propyl]-2,5-dioxo-1-imidazolidinyl]-, 1,1-dimethylethyl ester.

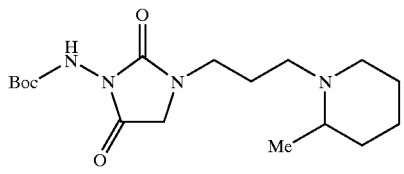

Carbamic acid, [2,5-dioxo-3-[3-(1-piperidinyl)propyl]-1-imidazolidinyl]-, 1,1-dimethylethyl ester.

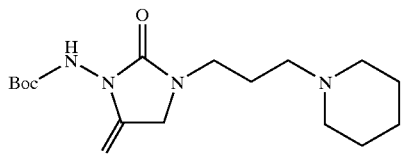

Carbamic acid, [3-[3-(4-morpholinyl)propyl]-2,5-dioxo-1-imidazolidinyl]-, 1,1-dimethylethyl ester.

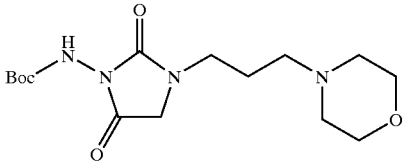

Carbamic acid, [2,5-dioxo-3-[3-(2-oxo-1-pyrrolidinyl)propyl]-1-imidazolidinyl]-, 1,1-dimethylethyl ester.

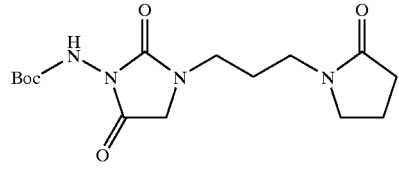

Carbamic acid, (3-[(6,6-dimethylbicyclo[3.1.1]hept-3-yl)methyl]-2,5-dioxo-1-imidazolidinyl]-, 1,1-dimethylethyl ester.

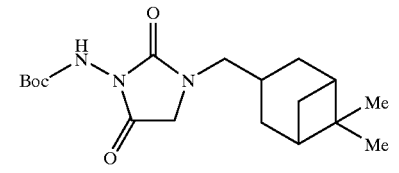

Carbamic acid, [2,5-dioxo-3-[1-(phenylmethyl)-4-piperidinyl]-1-imidazolidinyl]-, 1,1-dimethylethyl ester.

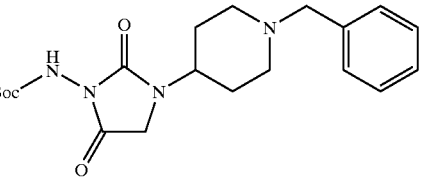

Carbamic acid, [3-[(4-methoxyphenyl)methyl]-5-oxo-2-thioxo-1-imidazolidinyl]-, 1,1-dimethylethyl ester.

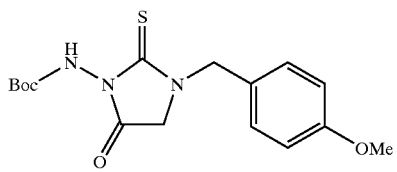

Carbamic acid, [tetrahydro-3-[(5-nitro-2-pyridinyl)amino]ethyl]-2,6-dioxo-1(2H)-pyrimidinyl]-, 1,1-dimethylethyl ester.

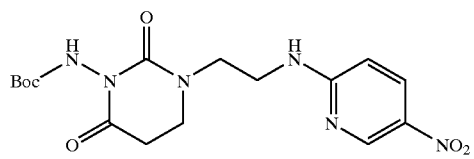

Carbamic acid, [tetrahydro-3-[2-(4-morpholinyl)ethyl]-2,6-dioxo-1(2H)-pyrimidinyl]-, 1,1-dimethylethyl ester.

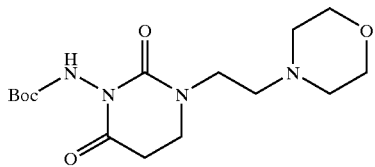

Carbamic acid, [tetrahydro-2,6-dioxo-3-[1-(phenylmethyl)-4-piperidinyl]-1(2H)-pyrimidinyl]-, 1,1-dimethylethyl ester.

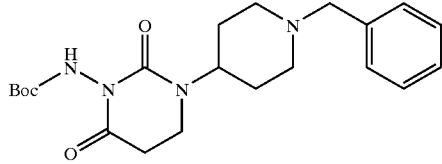

Solution-Phase Process for Making Compounds According to Formula I

In one embodiment, the present invention provides a one-pot solution-phase process for preparing compounds according to Formula I above depicted below as Scheme I. The process depicted below in Scheme I requires no chromatographies (for n=0) and a simple liquid/liquid extraction and crystallization/filtration at the end.

Scheme 1

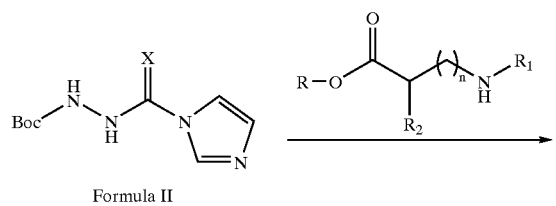

Formula II

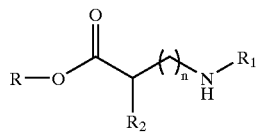

Formula I

The process depicted above in Scheme I begins with providing a compound according to Formula II. In Formula II, X is as defined above for Formula I. Compounds according to Formula II can be made from known starting materials and methods known to one of ordinary skill in the art. One particularly preferred method for the preparation of compounds according to Formula II involves slow addition of commercially available t-butoxycarbonyl (Boc) hydrazine to carbonyldiimidazole (X=O) or thiocarbonyldiimidazole (X=S). Once made, compounds according to Formula II need not be isolated, but rather can be reacted in situ for the next step.

Compounds according to Formula II are first reacted with amino acid esters having the following general structure:

$$R-O-\underset{O}{\overset{O}{\|}}\overset{R_2}{\underset{}{C}}(\ )_n-\underset{H}{N}-R_1$$

wherein $R_1$ and $R_2$ are as defined above for Formula I, and R is alkyl, carbocyclic ring, heterocyclic ring, aromatic ring, or heteroaromatic ring. Preferred R is methyl, ethyl, and benzyl. These amino acid esters are commercially available or are made from commercially available starting materials from methods known to one of ordinary skill in the art.

The resulting intermediates according to Sia need not be isolated, but rather undergo intramolecular cyclization to the desired products of Formula I on warning. Thus, the next step in the process is heating the reaction mixture. The preferred reaction time is 8 hours and the reaction temperature is preferably kept between 60–70° C. for 3-aminohydantoin derivatives (Formula I wherein n=0). The preferred reaction time is >24 hours and the reaction temperature is preferably kept between 100–110° C. for 3-aminodihydrouracil derivatives (Formula I wherein n=1). Commonly used organic solvents are used. Preferred organic solvents include THF, DMF, dioxane, and methylene chloride. The most preferred organic solvent is dioxane.

Solid-Phase Process for Making Compounds According to Formula I

In another embodiment, the present invention provides a solid-phase process for preparing compounds according to Formula Ia below. Formula Ia is a subset of Formula I compounds.

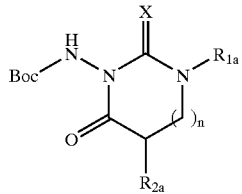

wherein

X is O or S;

n is 0 or 1;

$R_{1a}$ is H, alkyl, carbocyclic ring, heterocyclic ring, aromatic ring, or heteroaromatic ring;

$R_{2a}$ is H, alkyl, carbocyclic ring, heterocyclic ring, aromatic ring, or heteroaromatic ring;

The solid phase process is depicted below as Scheme II.

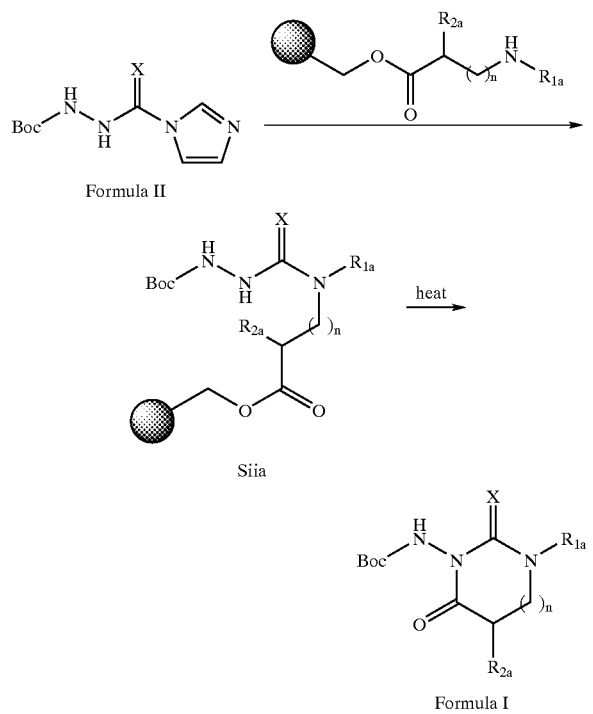

The process depicted above in Scheme II begins with providing a compound according to Formula II. Compounds according to Formula II are first reacted with resin-bound or amino acid esters having the following general structure:

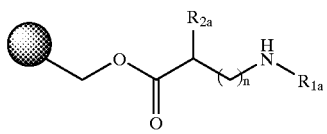

wherein $R_{1a}$ and $R_{2a}$ are as defined above for Formula I, and

is a Merrifield resin, hydroxymethyl resin, Wang resin, or PEG resin, preferably a Merrifield resin. These resin-bound or amino acid esters are made from commercially available starting materials from methods known to one of ordinary skill in the art. A preferred method for the preparation of Merrifield resin-bound or amino acid esters resins is to esterify the Merrifield resin with α-bromoacetic acid or acrylic acid. Relevant references include: Wilson, L. J.; Li, M.; Portlock, D. E. *Tetrahedron Lett.* 1998, 39 5135–5138. Morphy, J. R.; Rankovic, Z.; Rees, D. C. *Tetrahedron Lett.* 1996, 37 3209–3212. Kolodziej, S.; Hamper, B. C. *Tetrahedron Lett.* 1996, 37 5277–5280.

Compounds according to Formula II are preferably reacted with these resin-bound or amino acid esters at room temperature. Intermediates according to Siia are then thoroughly washed to remove impurities and excess reagents. In this reaction step, common organic solvents are used. Preferred organic solvents include THF, DMF, dioxane, acetonitrile and methylene chloride. The most preferred solvent is anhydrous DMF.

Warming compounds according to Siia induces intramolecular cyclization and release from the resin to provide the desired products according to Formula I. Thus, the next step in the process is heating the reaction mixture. The temperature of the cyclization reaction is preferably kept between about 60–70° C. and the reaction time is preferably about 8–10 hours for the formation of 3-aminohydantoin derivatives (Formula I, wherein n=0). The temperature of the cyclization reaction is preferably kept between about 90–95° C. and the reaction time is preferably 24 hours for the formation of 3-aminodihydrouracil derivatives (Formula I, wherein n=1).

This method allows for the ready preparation of 3-aminohydantoins/thiohydantoins and 3-aminodihydrouracils/dihydrothiouracils which contain a wide variety of substituents at N-1, including basic groups which can be difficult to purify when made by solution methods.

The following non-limiting examples illustrate the present invention:

EXAMPLE 1

Preparation of carbamic acid, [5-oxo-3-(phenylmethyl)-2-thioxo-1-imidazolidinyl]-, 1,1-dimethylethyl ester To a solution of 990 mg (90%, 5.0 mmol) of thiocarbonyldiimidazole in 25 mL of 1,4-dioxane is added dropwise 0.66 g (5 mmol) of tert-butyl carbazate in 25 mL of 1,4-dioxane. The solution is stirred for 3 hours at room temperature, followed by the addition of N-benzylglycine ethyl ester 996 mg (5 mmol). The resulting mixture is heated to 60° C. for 4 hours. The dioxane is removed under reduced pressure. The residue is dissolved in EtOAc (150 mL) and washed with water (2×50 mL), 0.1N aqueous HCl (2×50 mL), dried with $MgSO_4$ and concentrated in vacuo to afford carbamic acid, [5-oxo-3-(phenylmethyl)-2-thioxo-1-imidazolidinyl]-, 1,1-dimethylethyl ester (1.52 g, 95%).

EXAMPLE 2

Preparation of carbamic acid, [4-methyl-5-oxo-3-(phenylmethyl)-2-thioxo-1-imidazolidinyl]-, 1,1-dimethylethyl ester To a solution of 593 mg (90%, 3.0 mmol) of thiocarbonyldiimidazole in 15 mL of 1,4-dioxane is added dropwise 0.66 g (5 mmol) of tert-butyl carbazate in 25 mL of 1,4-dioxane. The solution is stirred for 3 hours at room temperature, followed by the addition of N-benzylalanine ethyl ester 621 mg (3 mmol). The resulting mixture is heated to 60° C. for 4 hours. The dioxane is removed under reduced pressure. The residue is dissolved in EtOAc (100 mL) and washed with water (50 mL), 0.1N aqueous HCl (2×25 mL), dried with $MgSO_4$ and concentrated in vacuo to afford carbamic acid, [4-methyl-5-oxo-3-(phenylmethyl)-2-thioxo-1-imidazolidinyl]-, 1,1-dimethylethyl ester (887 mg, 80%).

EXAMPLE 3

Preparation of carbamic acid, tetrahydro-5,7-dioxoimidazol[5,1-b]thiazol-6(5H)-yl-, 1,1-dimethyl ester To a solution of 1.03 g (6.4 mmol) of carbonyldiimidazole in 30 mL of THF is added dropwise 0.66 g (5 mmol) of tert-butyl carbazate in 10 mL of THF. The solution is stirred for 4 hours at room temperature, followed by the addition of methyl thiozolidine-2-carboxlate HCl salt 920 mg (5.0 mmol). The resulting mixture is heated to reflux for 4 hours. The THF is removed under reduced pressure. The residue is dissolved in EtOAc (100 mL) and washed with water (100 mL), 0.1N aqueous HCl (100 mL), water (100 mL), dried with $Na_2SO_4$ and concentrated in vacuo to afford carbamic acid, ((7aS)-tetrahydro-5,7-dioxoimidazol[5,1-b]thiazo-6(5H)-yl)-, 1,1-dimethylethyl ester (1.0 g, 74%).

EXAMPLE 4

Preparation of carbamic acid, ((10aS)-1,5,10,10a-tetrahydro-1,3-dioxoimidazol[1,5-b]isoquinolin-2(3H)-yl)-, 1,1-dimethylethyl ester To a solution of 1.06 g (6.5 mmol) of carbonyldiimidazole in 25 mL of 1,4-dioxane is added dropwise 0.66 g (5 mmol) of tert-butyl carbazate in 25 mL of 1,4-dioxane. The solution is stirred for 3 hours at room temperature, followed by the addition of benzyl (S)-(−) 1,2,3,4-tetrahydro-3-isoquinoline carboxylate p-toluenesulfonic acid salt 2.19 g (5 mmol) and triethylamine (0.5 mL). The resulting mixture is heated to 60° C. for 4 hours. The dioxane is removed under reduced pressure. The residue is dissolved in EtOAc (150 mL) and washed with water (2×50 mL), 0.1N aqueous HCl (2×50 mL), dried with $MgSO_4$ and concentrated to 20 mL in vacuo to give a white precipitate. The solid is filtered off and dried in vacuo to afford carbamic acid, ((10aS)-1,5,10,10a-tetrahydro-1,3-dioxoimidazol[1,5-b]isoquinolin-2(3H)-yl)-, 1,1-dimethylethyl ester (1.38 g, 87%).

EXAMPLE 5

Preparation of carbamic acid, ((10aS)-1,5,10,10a-tetrahydro-1-oxo-3-thioxoimidazol[1,5-b]isoquinolin-2(3H)-yl)-, 1,1-dimethylethyl ester To a solution of 972 mg (6 mmol) of carbonyldiimidazole in 25 mL of 1,4-dioxane is added dropwise 0.66 g (5 mmol) of tert-butyl carbazate in 25 mL of 1,4-dioxane. The solution is stirred for 3 hours at room temperature, followed by the addition of benzyl (S)-(−) 1,2,3,4-tetrahydro-3-isoquinoline carboxylate p-toluenesulfonic acid salt 2.19 g (5 mmol) and triethylamine (0.5 mL). The resulting mixture is heated to 60° C. for 4 hours. The dioxane is removed under reduced pressure. The residue is dissolved in EtOAc (150 mL) and washed with water (2×50 mL), 0.1N aqueous HCl (2×50 mL), dried with $MgSO_4$ and concentrated to 20 mL in vacuo to give a white precipitate. The solid is filtered off and dried in vacuo to afford carbamic acid, ((10aS)-1,5,10,10a-tetrahydro-1-oxo-3-thioxoimidazol[1,5-b]isoquinolin-2(3H)-yl)-, 1,1-dimethylethyl ester (1.56 g, 94%).

EXAMPLE 6

Preparation of carbamic acid, (2,5-dioxo-3-phenyl-1-imidazolidinyl)-, 1,1-dimethylethyl ester To a solution of 915 mg (5.6 mmol) of carbonyldiimidazole in 15 mL of 1,4-dioxane is added dropwise 528 g (4.8 mmol) of tert-butyl carbazate in 15 mL of 1,4-dioxane. The solution is stirred for 2 hours at room temperature, followed by the addition of N-phenyl glycinate ethyl ester 716 mg (4.0 mmol). The resulting mixture is heated to 70° C. for 7 hours. The dioxane is removed under reduced pressure. The residue is dissolved in EtOAc (100 mL) and washed with water (50 mL), 0.1N aqueous HCl (2×50 mL), dried with $MgSO_4$ and concentrated to 20 mL in vacuo to give a white precipitate. The solid is filtered off and dried in vacuo to afford Preparation of carbamic acid, (2,5-dioxo-3-phenyl-1-imidazolidinyl)-, 1,1-dimethylethyl ester (858 mg, 76%).

EXAMPLE 7

Preparation of carbamic acid, (5-oxo-3-phenyl-2-thioxo-1-imidazolidinyl)-, 1,1-dimethylethyl ester To a solution of 593 mg (3.0 mmol) of thiocarbonyldiimidazole in 15 mL of 1,4-dioxane is added dropwise 396 g (3.0 mmol) of tert-butyl carbazate in 15 mL of 1,4-dioxane. The solution is stirred for 3 hours at room temperature, followed by the addition of N-phenyl glycinate ethyl ester 495 mg (3.0 mmol). The resulting mixture is heated to 70° C. for 7 hours. The dioxane is removed under reduced pressure. The residue is dissolved in EtOAc (100 mL) and washed with water (50 mL), 0.1N aqueous HCl (2×50 mL), dried with $MgSO_4$ and concentrated to afford crude product which is further purified by Biotage column (eluent: EtOAc/Hexane, 3/7). The pure product, carbamic acid, (5-dioxo-3-phenyl-2-thioxo-1-imidazolidinyl)-, 1,1-dimethylethyl ester, is obtained as semisolid material (820 mg, 81%).

EXAMPLE 8

Preparation of carbamic acid, (hexahydro-1,3-dioxoimidazol[1,5-a]pyridin-2(3H)-yl)-, 1,1-dimethylethyl ester To a solution of 972 mg (6 mmol) of carbonyldiimidazole in 25 mL of 1,4-dioxane is added dropwise 792 g (6 mmol) of tert-butyl carbazate in 25 mL of 1,4-dioxane. The solution is stirred for 2 hours at room temperature, followed by the addition of ethyl pipecolinate 785 mg (5 mmol). The resulting mixture is heated to 60–70° C. for 4 hours. The dioxane is removed under reduced pressure. The residue is dissolved in EtOAc (150 mL) and washed with water (50 mL), 0.1N aqueous HCl (2×50 mL), dried with $MgSO_4$ and concentrated to afford carbamic acid, (hexahydro-1,3-dioxoimidazol[1,5-a]pyridin-2(3H)-yl)-, 1,1-dimethylethyl ester (1.21 g, 90%).

EXAMPLE 9

Preparation of carbamic acid, (3-(phenylmethyl)tetrahydro-2,6-dioxo-1(2H)-pyrimidinyl)-, 1,1-dimethylethyl ester To a solution of 1.14 g (7 mmol) of carbonyldiimidazole in 50 mL of 1,4-dioxane is added dropwise 793 mg (6 mmol)

of tert-butyl carbazate in 10 mL of 1,4-dioxane. The solution is stirred for 4 hours at room temperature, followed by the addition of N-benzyl--alanine ethyl ester 1.04 g (5 mmol). The resulting mixture is refluxed for 72 hours. The dioxane is removed under reduced pressure. The residue is dissolved in EtOAc, washed with $H_2O$, 0.1 N HCl, $H_2O$ respectively and dried over $Na_2SO_4$ and concentrated in vacuo to afford carbamic acid, (3-(phenylmethyl)tetrahydro-2,6-dioxo-1(2H)-pyrimidinyl)-, 1,1-dimethylethyl ester (1.02 g, 64%).

EXAMPLE 10

Preparation of carbamic acid, (3-(2-furanylmethyl) tetrahydro-6-oxo-2-thioxo-1(2H)-pyrimidinyl)-, 1,1-dimethylethyl ester To a solution of 988 mg (90%, 5.5 mmol) of thiocarbonyldiimidazole in 15 mL of 1,4-dioxane is added dropwise 660 mg (5 mmol) of tert-butyl carbazate in 25 mL of 1,4-dioxane. The solution is stirred for 3 hours at room temperature, followed by the addition of N-2-furanylmethyl--alanine ethyl ester 985 mg (5 mmol). The resulting mixture is refluxed for 24 hours. The dioxane is removed under reduced pressure. The residue is purified by Biotage column (eluent: EtOAc/Hexane, 6/4) to afford carbamic acid, (3-(2-furanylmethyl)tetrahydro-2-oxo-6-thioxo-1(2H)-pyrimidinyl)-, 1,1-dimethylethyl ester (1.25 g, 77%).

EXAMPLE 11

Preparation of carbamic acid, (3-(2-furanylmethyl) tetrahydro-2,6-dioxo-1(2H)-pyrimidinyl)-, 1,1-dimethylethyl ester To a solution of 810 mg (90%, 5.0 mmol) of carbonyldiimidazole in 25 mL of 1,4-dioxane is added dropwise 660 mg (5 mmol) of tert-butyl carbazate in 25 mL of 1,4-dioxane. The solution is stirred for 3 hours at room temperature, followed by the addition of N-2-furanylmethyl-alanine ethyl ester 985 mg (5 mmol). The resulting mixture is refluxed for 24 hours. The dioxane is removed under reduced pressure. The residue is purified by Biotage column (eluent: EtOAc/Hexane, 6/4) to afford carbamic acid, (3-(2-furanylmethyl)tetrahydro-2,6-dioxo-1(2H)-pyrimidinyl)-, 1,1-dimethylethyl ester (1.01 g, 65%).

EXAMPLE 12

Preparation of carbamic acid, (3-butyltetrahydro-6-oxo-2-thioxo-1(2H)-pyrimidinyl)-, 1,1-dimethylethyl ester To a solution of 984 mg (90%, 5.5 mmol) of thiocarbonyldiimidazole in 25 mL of 1,4-dioxane is added dropwise 0.66 g (5 mmol) of tert-butyl carbazate in 25 mL of 1,4-dioxane. The solution is stirred for 3 hours at room temperature, followed by the addition of N-n-butyl--alanine methyl ester 795 mg (5 mmol). The resulting mixture is refluxed for 24 hours. The dioxane is removed under reduced pressure. The residue is dissolved in EtOAc (100 mL) and washed with water (50 mL), 0.1N aqueous HCl (2×25 mL), dried with $MgSO_4$ and concentrated in vacuo to afford carbamic acid, (3-butyltetrahydro-6-oxo-2-thioxo-1(2H)-pyrimidinyl)-, 1,1-dimethylethyl ester (1.23 g, 81%).

EXAMPLE 13

Preparation of carbamic acid, (3-butyltetrahydro-2,6-dioxo-1(2H)-pyrimidinyl)-, 1,1-dimethylethyl ester To a solution of 1.14 g (7.0 mmol) of carbonyldiimidazole in 30 mL of 1,4-dioxane is added dropwise 0.79 g (6 mmol) of tert-butyl carbazate in 20 mL of 1,4-dioxane. The solution is stirred for 4 hours at room temperature, followed by the addition of N-n-butyl- -alanine methyl ester 795 mg (5 mmol). The resulting mixture is refluxed for 40 hours. The dioxane is removed under reduced pressure. The residue is dissolved in EtOAc, washed with $H_2O$, 0.1 N HCl, $H_2O$ respectively and dried over $Na_2SO_4$ and concentrated in vacuo to afford carbamic acid, (3-butyltetrahydro-2,6-dioxo-1(2H)-pyrimidinyl)-, 1,1-dimethylethyl ester (1.28 g, 84%).

EXAMPLE 14

Preparation of carbamic acid, (tetrahydro-6-oxo-3-(4-methoxyphenyl)-2-thioxo-1(2H)-pyrimidinyl)-, 1, 1-dimethylethyl ester To a solution of 988 mg (90%, 5.5 mmol) of thiocarbonyldiimidazole in 25 mL of 1,4-dioxane is added dropwise 0.66 g (5 mmol) of tert-butyl carbazate in 25 mL of 1,4-dioxane. The solution is stirred for 3 hours at room temperature, followed by the addition of N-(4-methoxyphenyl)- -alanine ethyl ester 1.12 g (5 mmol). The resulting mixture is refluxed for 48 hours. The dioxane is removed under reduced pressure. The residue is dissolved in EtOAc (100 mL) and washed with water (50 mL), 0.1N aqueous HCl (2×25 mL), dried with $MgSO_4$ and concentrated in vacuo to afford carbamic acid, (tetrahydro-6-oxo-3-(4-methoxyphenyl)-2-thioxo-1(2H)-pyrimidinyl)-, 1,1-dimethylethyl ester (0.59 g, 33%).

EXAMPLE 15

Preparation of Merrifield resin-bound -bromoacetate ester

To a solution of DIC (diisopropylcarbodiimide) (31 g, 253 mmol), -bromoacetic acid (35 g, 246 mmol) and Merrifield resin (50 g, 33.5 mmol, loading level: 0.67 mmol/g) in methylene chloride (600 mL) is added DMAP (1 g, 8.1 mmol). The resulting mixture is shaken at room temperature for 24 hours. Resin is collected on a glass filter and washed two times each with DMF, MeOH, DCM. The resin is dried to give the Merrifield resin-bound -bromoacetate ester (53.1 g, yield 98%).

EXAMPLE 16

Preparation of carbamic acid, [2,5-dioxo-3-[2-(2-pyridinyl)ethyl]-1-imidazolidinyl]-, 1,1-dimethylethyl ester Merrifield resin-bound -bromoacetate ester (2 g, loading 0.67 mmol/g) is treated with DMF (40 mL) and 2-(2-aminoethyl)pyridine (810 mg, 6.6 mmol) and allowed to shake for 24 hours at room temperature. Washing two times each with DMF, MeOH, DCM afforded resin. This is then treated with Boc-hydrazinecarbonylimidazole (6.6 mmol) in 40 mL of DMF (prepared in situ according to the process of solution-phase chemistry which is described above in Scheme 1) at room temperature for 10 hours and washed two times each with DMF, MeOH, DCM to afford a resin according to Siia (where n=0, X=O, $R_1$=2-(2-pyridinyl) ethyl). The resin is then placed in a flask with 40 mL of DMF and heated to 65–70° C. for 8 hours. After cooling, the resin is filtered, washed with small amount of DMF, DCM and MeOH and the combined filtrates concentrated. The residue is dissolved in 30 mL of MeOH and filtered, concentrated in vacuo to give desired product, carbamic acid, [2,5 dioxo-3-[2-(2-pyridinyl)ethyl]-1-imidazolidinyl], 1,1-dimethylethyl ester (183 mg, 63%).

EXAMPLE 17

Preparation of carbamic acid, [3-[2-(5-methoxy-1H-indol-3-yl)ethyl]-2,5-dioxo-1-imidazolidinyl]-, 1,1-dimethylethyl ester Merrifield resin-bound -bromoacetate ester (2 g, loading 0.67 mmol/g) is treated with DMSO (60 mL) and 5-methoxytryptamine (1.0 g, 5.26 mmol) and allowed to shake for 24 hours at room temperature. Washing two times each with DMF, MeOH, DCM affords the resin. This is then treated with Boc-hydrazinecarbonylimidazole (5.2 mmol) in 60 mL of DMF (prepared in situ according to the process of solution-phase chemistry which is described above in Scheme 1) at room temperature for 10 hours and washed two times each with DMF, MeOH, DCM to afford a resin according to Siia (where n=0, X=O, $R_1$=2-(5-methoxy-1H-indol-3-yl)ethyl). The resin is then placed in a flask with 50 mL of DMF and heated to 60–70° C. for 8 hours. After cooling, the resin is filtered, washed two times each with DMF, DCM and MeOH and the combined filtrates concentrated. The residue is dissolved in 30 mL of MeOH and filtered, concentrated in vacuo to give desired product, carbamic acid, [3-[2-(5-methoxy-1H-indol-3-yl)ethyl]-2,5-dioxo-1-imidazolidinyl]-, 1,1-dimethylethyl ester (310 mg, 61%).

EXAMPLE 18

Preparation of carbamic acid, [3-[2-(1H-imidazol-4-yl)-ethyl]-2,5-dioxo-1-imidazolidinyl]-, 1,1-dimethylethyl ester Merrifield resin-bound -bromoacetate ester (2 g, loading 0.67 mmol/g) is treated with DMSO (60 mL) and histamine (733 mg, 6.6 mmol) and allowed to shake for 24 hours at room temperature. Washing two times each with DMF, MeOH, DCM afford the resin. This is then treated with Boc-hydrazinecarbonylimidazole (6.6 mmol) in 60 mL of DMF (prepared in situ according to the process of solution-phase chemistry which is described above in Scheme 1) at room temperature for 10 hours and washed two times each with DMF, MeOH, DCM to afford a resin according to Siia (where n=0, X=O, $R_1$=2-(1H-imidazol-4-yl)-ethyl). The resin is then placed in a flask with 50 mL of DMF and heated to 60–70° C. for 8 hours. After cooling, the resin is filtered, washed with small amount of DMF, DCM and MeOH and the combined filtrates concentrated. The residue is dissolved in 30 mL of MeOH and filtered, concentrated in vacuo to give desired product, carbamic acid, [3-[2-(1H-imidazol-4-yl)-ethyl]-2,5-dioxo-1-imidazolidinyl]-, 1,1-dimethylethyl ester (202 mg, 50%).

EXAMPLE 19

Preparation of carbamic acid, [3-[2-(1-methyl-2-pyrrolidinyl)ethyl]-2,5-dioxo-1-imidazolidinyl]-, 1,1-dimethylethyl ester The Merrifield resin-bound -bromoacetate ester (3 g, loading 0.67 mmol/g) is treated with DMSO (60 mL) and 2-(2-aminoethyl)-1-methylpyrrolidine (1.42 g, 10 mmol) and allowed to shake for 24 hours at room temperature. Washing two times each with DMF, MeOH, DCM affords the resin. This is then treated with Boc-hydrazinecarbonylimidazole (10 mmol) in 60 mL of DMF (prepared in situ according to the process of solution-phase chemistry which is described above in Scheme 1) at room temperature for 10 hours and washed two times each with DMF, MeOH, DCM to afford a resin according to Siia (where n=0, X=O, $R_1$=2-(1-methyl-2-pyrrolidinyl)ethyl). The resin is then placed in a flask with 50 mL of DMF and heated to 60–70° C. for 8 hours. After cooling, the resin is filtered, washed with small amount of DMF, DCM and MeOH and the combined filtrates concentrated. The residue is dissolved in 30 mL of MeOH and filtered, concentrated in vacuo to give desired product (445 mg, 69%).

EXAMPLE 20

Preparation of carbamic acid, [3-[2-[[5-nitro-2-pyridinyl]amino]ethyl]-2,5-dioxo-1-imidazolidinyl]-, 1,1-dimethylethyl ester Merrifield resin-bound -bromoacetate ester (3 g, loading 0.67 mmol/g) is treated with DMSO (60 mL) and 2-(2-aminoethylamino)-5-nitropyridine (1.82 g, 10 mmol) and allowed to shake for 24 hours at room temperature. Washing two times each with DMF, MeOH, DCM affords the resin. This is then treated with Boc-hydrazinecarbonylimidazole (10 mmol) in 60 mL of DMF (prepared in situ according to the process of solution-phase chemistry which is described above in Scheme 1) at room temperature for 10 hours and washed two times each with DMF, MeOH, DCM to afford a resin according to Siia (where n=0, X=O, $R_1$=2-[[5-nitro-2-pyridinyl]amino]ethyl). The resin is then place in a flask with 50 mL of DMF and heated to 60–70° C. for 8 hours. After cooling, the resin is filtered, washed two times each with DMF, DCM and MeOH and the combined filtrates concentrated. The residue is dissolved in 30 mL of MeOH and filtered, concentrated in vacuo to give desired product, carbamic acid, [3-[2-[[5-nitro-2-pyridinyl]amino]ethyl]-2,5-dioxo-1-imidazolidinyl]-, 1,1-dimethylethyl ester (440 mg, 58.5%).

EXAMPLE 21

Preparation of carbamic acid, [2,5-dioxo-3-[2-(1-piperidinyl)ethyl]-1-imidazolidinyl]-, 1,1-dimethylethyl ester Merrifield resin-bound -bromoacetate ester (2 g, loading 0.67 mmol/g) is treated with DMSO (60 mL) and 1-(2-aminoethyl)piperidine (0.88 g, 6.7 mmol) and allowed to shake for 24 hours at room temperature. Washing two times each with DMF, MeOH, DCM affords the resin. This is then treated with Boc-hydrazinecarbonylimidazole (6.5 mmol) in 50 mL of DMF (prepared in situ according to the process of solution-phase chemistry which is described above in Scheme 1) at room temperature for 10 hours and washed two times each with DMF, MeOH, DCM to afford a resin according to Siia (where n=0, X=O, $R_1$=2-(1-piperidinyl)ethyl). The resin is then placed in a flask with 30 mL of DMF and heated to 60–70° C. for 8 hours. After cooling, the resin is filtered, washed two times each with DMF, DCM and MeOH and the combined filtrates concentrated. The residue is dissolved in 30 mL of MeOH and filtered, concentrated in vacuo to give desired product, carbamic acid, [2,5-dioxo-3-[2-(1-piperidinyl)ethyl]-1-imidazolidinyl]-, 1,1-dimethylethyl ester (262 mg, 59%).

EXAMPLE 22

Preparation of Merrifield resin-bound acrylate ester

To a solution of DIC (15 g, 119 mmol), acrylic acid (17 g, 208 mmol) and Merrifield resin (25 g, 200 mmol, loading level: 0.80 mmol/g) in methylene chloride (300 mL) is added DMAP (0.5 g, 4 mmol). The resulting mixture is shaken at room temperature for 24 hours. Resin is collected on a glass filter and washed two times each with DMF, MeOH, DCM. The resin is dried to give the Merrifield resin-bound acrylate ester (37 g, yield 94%).

EXAMPLE 23

Preparation of carbamic acid, [tetrahydro-3-[(5-nitro-2-pyridinyl)amino]ethyl]-2,6-dioxo-1(2H)-pyrimidinyl]-, 1,1-dimethylethyl ester Merrifield resin-bound acrylate ester (2 g, loading 0.8 mmol/g) is treated with DMSO (50 mL) and 2-(2-aminoethylamino)-5-nitropyridine (1.46 g, 8.0 mmol) and allowed to shake for 24 hours at room temperature. Washing two times each with DMF, MeOH, DCM affords the resin. This is then treated with Boc-hydrazinecarbonylimidazole (8 mmol) in 40 mL of DMF (prepared in situ according to the process of solution-phase chemistry which is described above in Scheme 1) at room temperature for 24 hours and washed two times each with DMF, MeOH, DCM to afford a resin according to Siia (where n=1, X=O, $R_1$=(5-nitro-2-pyridinyl)aminoethyl). The resin is then placed in a flask with 40 mL of DMF and heated to 95° C. for 24 hours. After cooling, the resin is filtered, washed two times each with DMF, DCM and MeOH and the combined filtrates concentrated. The residue is dissolved in 40 mL of EtOAc and filtered, concentrated in vacuo to give desired product carbamic acid, [tetrahydro-3-[(5-nitro-2-pyridinyl)amino]ethyl]-2,6-dioxo-1(2H)-pyrimidinyl]-, 1,1-dimethylethyl ester (289 mg, 46%).

EXAMPLE 24

Preparation of carbamic acid, [tetrahydro-3-[2-(4-morpholinyl)ethyl]-2,6-dioxo-1(2H)-pyrimidinyl]-, 1,1-dimethylethyl ester Merrifield resin-bound acrylate ester (2 g, loading, 8.0 mmol/g) is treated with DMSO (50 mL) and 4-(2-aminoethyl)morpholine (1.04 g, 8 mmol) and allowed to shake for 24 hours at room temperature. Washing two times each with DMF, MeOH, DCM affords the resin. This is then treated with Boc-hydrazinecarbonylimidazole (8 mmol) in 40 mL of DMF (prepared in situ according to the process of solution-phase chemistry which is described above in Scheme 1) at room temperature for 24 hours and washed two times each with DMF, MeOH, DCM to afford a resin according to Siia (where n=1, X=O, $R_1$=2-(4-morpholinyl)ethyl). The resin is then placed in a flask with 40 mL of DMF and heated to 95° C. for 24 hours. After cooling, the resin is filtered, washed two times each with DMF, DCM and MeOH and the combined filtrates concentrated. The residue is dissolved in 40 mL of EtOAc and filtered, concentrated in vacuo to give desired product carbamic acid, [tetrahydro-3-[2-(4-morpholinyl)ethyl]-2,6-dioxo-1(2H)-pyrimidinyl]-, 1,1-dimethylethyl ester (229 mg, 42%).

EXAMPLE 25

Preparation of carbamic acid, [tetrahydro-2,6-dioxo-3-[1-(phenylmethyl)-4-piperidinyl]-1(2H)-pyrimidinyl]-, 1,1-dimethylethyl ester Merrifield resin-bound acrylate ester (2 g, loading, 8.0 mmol/g) is treated with DMSO (50 mL) and 4-amino-1-benzyl-piperidine (1.52 g, 8 mmol) and allowed to shake for 24 hours at room temperature. Washing two times each with DMF, MeOH, DCM affords the resin. This is then treated with Boc-hydrazinecarbonylimidazole (8 mmol) in 40 mL of DMF (prepared in situ according to the process of solution-phase chemistry which is described above in Scheme 1) at room temperature for 24 hours and washed two times each with DMF, MeOH, DCM to afford a resin according to Siia (where n=1, X=O, $R_1$=1-(phenylmethyl)-4-piperidinyl). The resin is then placed in a flask with 40 mL of DMF and heated to 95° C. for 24 hours. After cooling, the resin is filtered, washed two times each with DMF, DCM and MeOH and the combined filtrates concentrated. The residue is dissolved in 20–30 mL of MeOH and filtered, concentrated in vacuo to give desired product carbamic acid, [tetrahydro-2,6-dioxo-3-[1-(phenylmethyl)-4-piperidinyl]-1(2H)-pyrimidinyl]-, 1,1-dimethylethyl ester (289 mg, 45%).

EXAMPLE 26

Preparation of carbamic acid, [tetrahydro-6-oxo-3-(phenylmethyl)-2-thioxo-1(2H)-pyrimidinyl]-, 1,1-dimethylethyl ester Merrifield resin-bound acrylate ester (2 g, loading, 8.0 mmol/g) is treated with DMSO (50 mL) and benzyl amine (1.025 g, 9 mmol) and allowed to shake for 24 hours at room temperature. Washing two times each with DMF, MeOH, DCM affords the resin. This is then treated with Boc-hydrazinecarbonylimidazole (6 mmol) in 50 mL of DMF (prepared in situ according to the process of solution-phase chemistry which is described above in Scheme 1) at room temperature for 24 hours and washed two times each with DMF, MeOH, DCM to afford a resin according to Siia (where n=1, X=S, $R_1$=benzyl). The resin is then placed in a flask with 50 mL of DMF and heated to 95° C. for 24 hours. After cooling, the resin is filtered, washed two times each with DMF, DCM and MeOH and the combined filtrates concentrated. The residue is dissolved in 40 mL of EtOAc and filtered, concentrated in vacuo to give desired product carbamic acid, [tetrahydro-6-oxo-3-(phenylmethyl)-2-thioxo-1(2H)-pyrimidinyl]-, 1,1-dimethylethyl ester (117 mg, 22%).

What is claimed is:

1. A method for making a hydantoin or thiohydantoin having the formula:

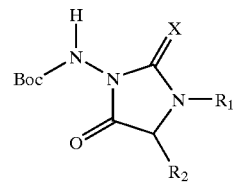

wherein X is oxygen or sulfur, $R_1$ is hydrogen, alkyl, a heterocyclic ring, an aromatic ring, or a heteroaromatic ring; $R_2$ is hydrogen, alkyl, a heterocyclic ring, an aromatic ring, or a heteroaromatic ring; said method comprising the steps of:

a) reacting a hydrazine compound having the formula:

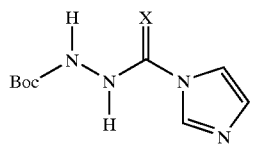

with an amino acid ester having the formula:

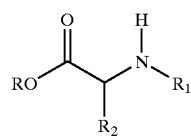

R is alkyl, carbocyclic ring, heterocyclic ring, aromatic ring, or heteroaromatic ring, to form a reaction mixture; and b) heating said reaction mixture to form said hydantoin or thiohydantoin.

2. A method according to claim 1 wherein X is oxygen.

3. A method according to claim 1 wherein said $R_1$ is a unit selected from the group consisting of phenyl, 4-methoxyphenyl, benzyl, 4-methoxybenzyl, 2-furanylmethyl, 1,3-benzodioxol-5-ylmethyl, (5-methoxy-1H-indol-3-yl)ethyl, (1H-imidazol-1-yl)ethyl, (1H-imidazol-4-yl)ethyl, [(5-nitro-2-pyridinyl)amino]ethyl, 2-(1-piperidinyl)ethyl, (1-methyl-2-pyrrolidinyl)ethyl, (2-methyl-1-piperidinyl)propyl, 3-(1-piperidinyl)propyl, 3-(4-morpholinyl)propyl, 3-(2-oxo-1-pyrrolidinyl)propyl, (6,6-dimethylbicyclo[3.1.1]hept-3-yl)methyl, 1-(phenylmethyl)-4-piperidinyl, and 2-furanylmethyl.

4. A method according to claim 1 wherein said amino acid ester is selected from the group consisting of a benzyl, methyl, or ethyl ester of 2-pipecoline carboxylate, proline, 4-hydroxyproline, 1,2,3,4-tetrahydro-3-isoquinolinecarboxylate, thiozolidine-2-carboxylate, and mixtures thereof.

5. A method according to claim 1 wherein $R_2$ is hydrogen or methyl.

6. A method according to claim 1 wherein said process is conducted in the presence of a solvent selected from the group consisting of tetrahydrofuran, dimethylformamide, dioxane, methylene chloride, and mixtures thereof.

7. A method according to claim 1 wherein step (b) is conducted at a temperature of from 60° C. to 70° C.

8. A method according to claim 1 wherein prior to step (a) said process comprises a step of forming said hydrazine compound having the formula:

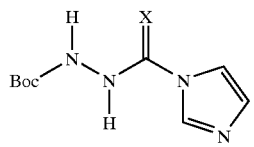

wherein said step comprises reacting tert-butoxycarbonyl hydrazine with carbonyldiimidazole or thiocarbonyldiimidazole to form said hydrazine compound.

9. A method according to claim 8 wherein said hydrazine compound is used in step (a) directly without further purification.

10. A method according to claim 1 further comprising the step of isolating said hydantoin or thiohydantoin.

11. A method according to claim 6 wherein said process further comprises the step of removing said solvent.

12. A method according to claim 1 wherein prior to step (a) said process comprises a step of forming said hydrazine compound having the formula:

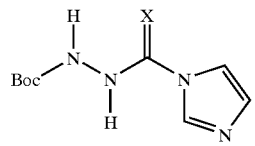

wherein said step comprises reacting tert-butoxycarbonyl hydrazine with carbonyldiimidazole or thiocarbonyldiimidazole to form said hydrazine compound.

13. A method according to claim 12 wherein said hydrazine compound is used in step (a) directly without further purification.

14. A method for making a 3-aminodihydrouracil or 3-aminodihydrothiouracil having the formula:

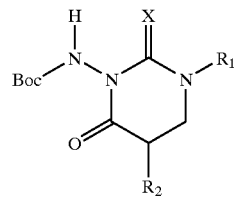

wherein X is oxygen or sulfur, $R_1$ is hydrogen, alkyl, a heterocyclic ring, an aromatic ring, or a heteroaromatic ring; $R_2$ is hydrogen, alkyl, a heterocyclic ring, an aromatic ring, or a heteroaromatic ring; or $R_1$ and the member carbon atom adjacent to the carbon atom containing $R_2$ can be taken together to form a ring system; said ring system being carbocyclic ring, heterocyclic ring, or heteroaromatic ring; said method comprising the steps of:

a) reacting a hydrazine compound having the formula:

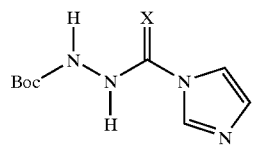

with an amino acid ester having the formula:

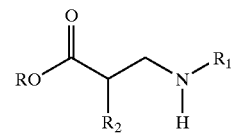

R is alkyl, carbocyclic ring, heterocyclic ring, aromatic ring, heteroaromatic ring, to form a reaction mixture; and b) heating said reaction mixture to form said 3-aminodihydrouracil or 3-aminodihydrothiouracil.

15. A method according to claim 14 wherein X is oxygen.

16. A method according to claim 14 wherein said $R_1$ is a unit selected from the group consisting of phenyl, 4-methoxyphenyl, benzyl, 4-methoxybenzyl, 2-furanylmethyl, 1,3-benzodioxol-5-ylmethyl, (5-methoxy-1H-indol-3-yl)ethyl, (1H-imidazol-1-yl)ethyl, (1H- imidazol-4-yl)ethyl, [(5-nitro-2-pyridinyl)amino]ethyl, 2-(1-piperidinyl)ethyl, (1-methyl-2-pyrrolidinyl)ethyl, (2-methyl-1-piperidinyl)propyl, 3-(1-piperidinyl)propyl, 3-(4-morphilinyl)propyl, 3-(2-oxo-1-pyrrolidinyl)propyl, (6,6-dimethylbicyclo[3.1.1]hept-3-yl)methyl, 1-(phenylmethyl)-4-piperidinyl, and 2-furanylmethyl.

17. A method according to claim 14 wherein said amino acid ester is selected from the group consisting of a benzyl, methyl, or ethyl ester of 2-pipecoline carboxylate, proline, 4-hydroxyproline, 1,2,3,4-tetrahydro-3-isoquinolinecarboxylate, thiozolidine-2-carboxylate, and mixtures thereof.

18. A method according to claim 14 wherein $R_2$ is hydrogen or methyl.

19. A method according to claim 14 wherein said process is conducted in the presence of a solvent selected from the group consisting or tetrahydrofuran, dimethylformamide, dioxane, methylene chloride, and mixtures thereof.

20. A method according to claim 19 wherein said solvent is dioxane.

21. A method according to claim 14 wherein step (b) is conducted at a temperature of from 100° C. to 110° C.

22. A method according to claim 14 further comprising the step of isolating said hydantoin or thiohydantoin.

23. A method according to claim 19 wherein said process further comprises the step of removing said solvent.

24. A method for making a hydantoin or thiohydantoin having the formula:

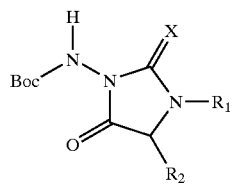

wherein X is oxygen or sulfur, $R_1$ is hydrogen, alkyl, a heterocyclic ring, an aromatic ring, or a heteroaromatic ring; $R_2$ is hydrogen, alkyl, a heterocyclic ring, an aromatic ring, or a heteroaromatic ring; or $R_1$ and $R_2$ can be taken together to form a carbocyclic ring, heterocyclic ring, with the hydantoin a heteroaromatic ring with the hydantoin or; said method comprising the steps of:

a) relating a hydrazine compound having the formula:

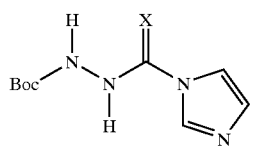

with a resin-bound amino acid ester having the formula

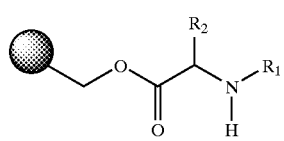

wherein the symbol:

signifies a Merrifield resin, hydroxymethyl, resin, Wang resin, or PEG resin: to form a reaction mixture; and b) heating said reaction mixture to form said hydantoin or thiohydantoin.

25. A method for making a 3-aminodihydrouracil or 3-aminodihydrothiouracil having the formula:

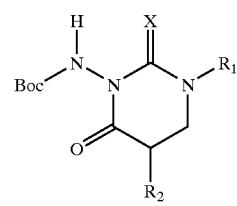

wherein X is oxygen or sulfur, $R_1$ is hydrogen, alkyl, a heterocyclic ring, an aromatic ring, or a heteroaromatic ring; $R_2$ is hydrogen, alkyl, a heterocyclic ring, an aromatic ring, or a heteroaromatic ring; or $R_1$ and the member carbon atom adjacent to the carbon atom containing $R_2$ can be taken together to form a carbocyclic ring, heterocyclic ring, a with the 3-aminodihydrouracil or 3-heteroaromatic ring with the 3-aminodihydrouracil or; said method comprising the steps of:

a) reacting a hydrazine compound having the formula:

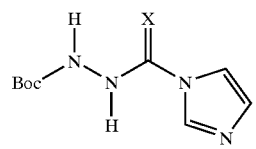

with an amino acid ester having the formula:

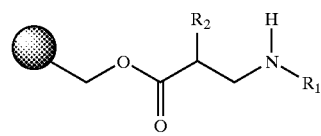

wherein the symbol:

signifies a Merrifield resin, hydroxymethyl, resin, Wang resin, or PEG resin; to form a reaction mixture; and b) heating said reaction mixture to form said 3-aminodihydrouracil or 3-aminodihydrothiouracil.

* * * * *